United States Patent [19]

Robinson

[11] Patent Number: 5,224,495
[45] Date of Patent: Jul. 6, 1993

[54] SUN AND SOUND SHIELDING ARRANGEMENT

[76] Inventor: James H. Robinson, 11602 W. 71 Ave., Arvada, Colo. 80004

[21] Appl. No.: 841,162

[22] Filed: Feb. 25, 1992

[51] Int. Cl.$^5$ .............................................. A61H 15/00
[52] U.S. Cl. ...................................... 128/857; 2/177; 2/209; 128/867
[58] Field of Search ............... 2/422, 423, 12, 177, 2/209, 196, 185 R; 128/867, 858, 857

[56] References Cited

U.S. PATENT DOCUMENTS

| | | | |
|---|---|---|---|
| 3,330,051 | 7/1967 | Pambello | 2/12 |
| 3,651,847 | 3/1972 | Casamassima | 2/177 |
| 3,922,721 | 12/1975 | Gales | 2/209 |
| 4,461,290 | 7/1984 | Gardner, Jr. et al. | 128/152 |
| 4,490,857 | 1/1985 | Leight et al. | 2/209 |
| 4,671,265 | 6/1987 | Anderson | 128/152 |
| 4,819,624 | 4/1989 | Leight et al. | 128/866 |
| 4,944,361 | 7/1990 | Lindgren | 2/423 |

FOREIGN PATENT DOCUMENTS 1069146  7/1965  United Kingdom .................... 2/424

Primary Examiner—Robert A. Hafer
Assistant Examiner—David J. Kenealy
Attorney, Agent, or Firm—Henderson & Sturm

[57] ABSTRACT

A sun and sound shielding arrangement (10) for allowing a person to sleep in a bright noisy environment wherein the arrangement (10) includes a sun shade member (20) having an open end box configuration provided with air flow openings (24); and, an ear plug unit (11) including ear plug members (13) mounted on a spring element (14) such that the ear plug members (13) will cause the tragus (101) of the user's ear (100) to block the auditory canals (102).

3 Claims, 1 Drawing Sheet

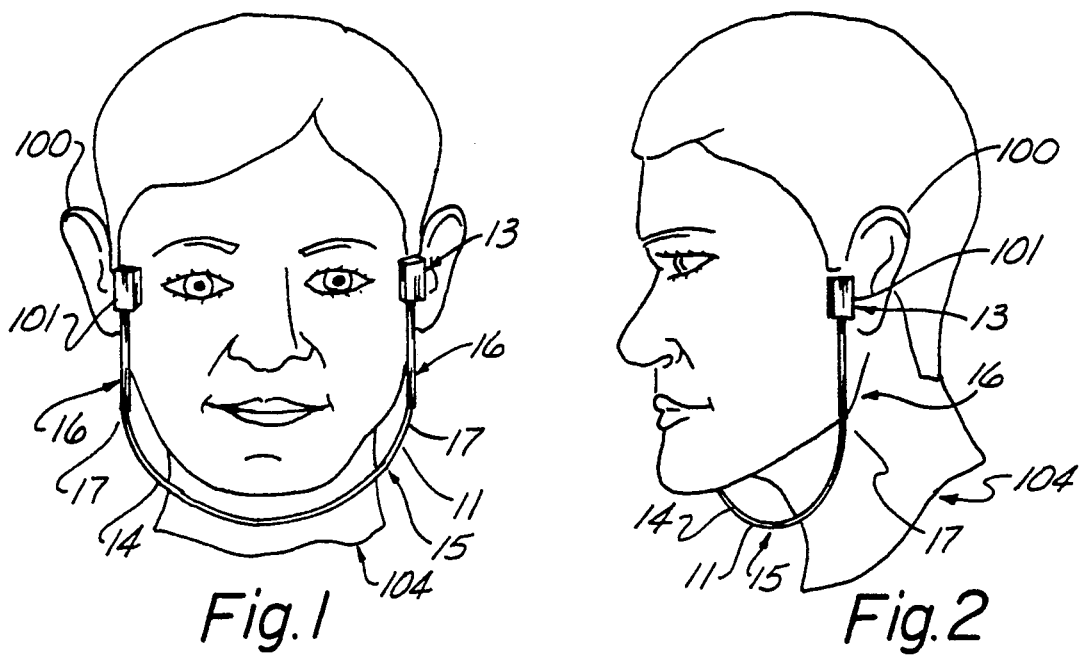
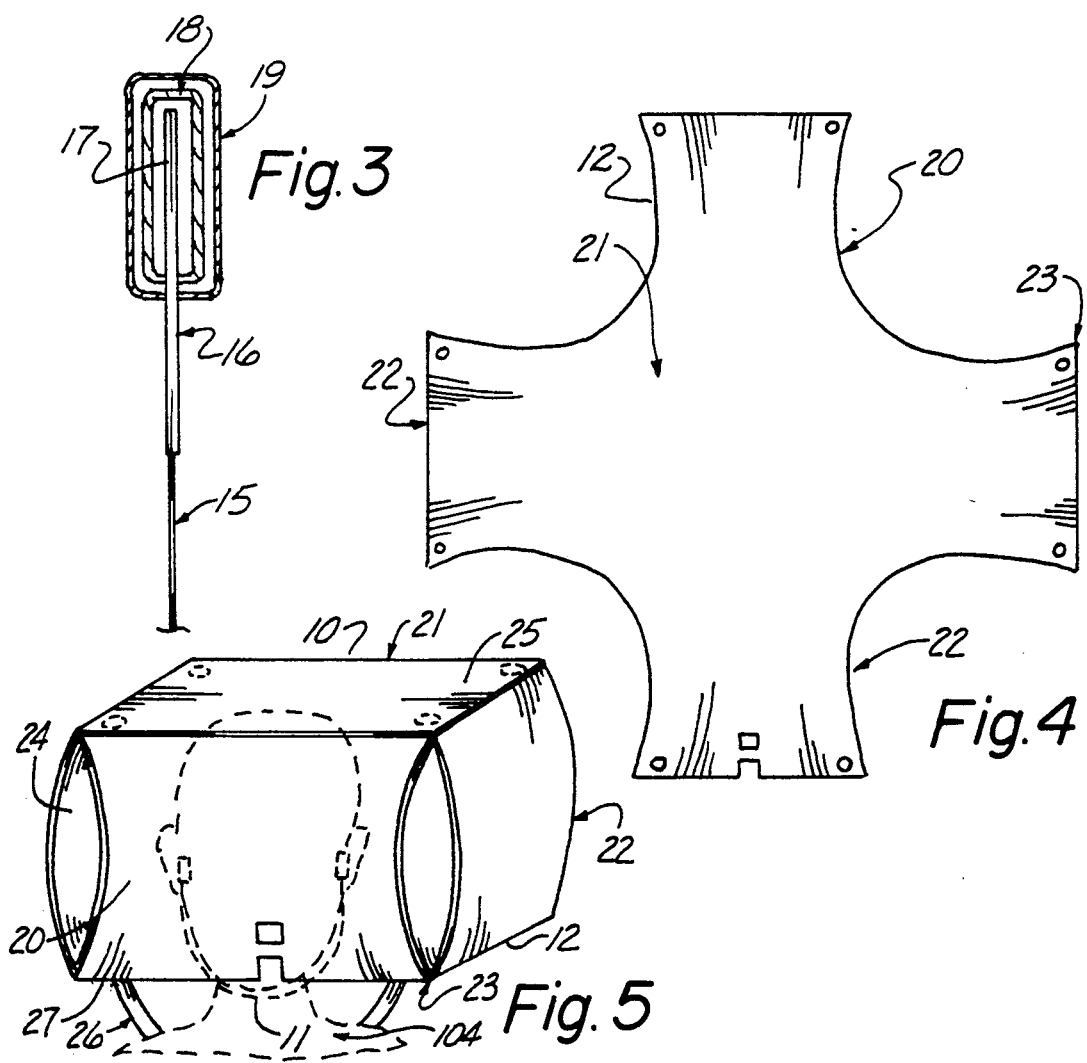

SUN AND SOUND SHIELDING ARRANGEMENT

TECHNICAL FIELD

The present invention relates to the field of sleep aids in general, and in particular to a combined system for blocking out both sound and the direct rays of the sun such as would be encountered at a beach or the like.

BACKGROUND ART

As can be seen by reference to the following U.S. Pat. Nos. 4,819,624; 4,671,265; 4,461,290; and 4,490,857; the prior art is replete with myriad and diverse ear plug constructions which are designed to block out unwanted noise for a variety of reasons.

While all of the aforementioned prior art constructions are more than adequate for the basic purpose and function for which they have been specifically designed, these patented structures are also uniformly deficient with regard to the fact that they all require that plugs are inserted into the auditory canal of the user. Not only does this fact require that the plugs be maintained free of dirt and other contaminants to prevent the users ears from becoming infected; but, it also necessitates that the plugs be wiped clean after each use to remove the accumulated ear wax that has been deposited on the ear plugs.

However, the elimination of sound forms only a portion of the present invention which is designed to block out both sun and sound so as to allow a person to sleep outdoors in sunny weather. The other component of this invention being a sun shield which provides shade while still allowing for ample airflow around the users head when both the earplugs and the sun shade are deployed in their operative disposition.

As a consequence of the foregoing situation, there has existed a longstanding need for both a new type of earplug which employs a portion of the users ears to block sound as well as a sun shade that will block the direct rays of the sun from impinging on a persons eyes to facilitate sleeping in a sunny and noisy environment; and, the provision of such a construction is a stated objective of the present invention.

DISCLOSURE OF THE INVENTION

Briefly stated, the sun and sound shielding arrangement that forms the basis of the present invention comprises a sun shield unit and an ear plug unit which when employed in combination with one another block out the two most significant reasons why people find it difficult to sleep (i.e. light and noise.)

The sun shield unit of this invention comprises an open box like shade producing member having open edges to allow air to circulate around the users head when the user is wearing the sun shield member. In addition the shade producing member is further provided with a reflective coating which not only keeps the interior of the sun shield member cool but also provides opacity to the sun shield member.

As will be explained in greater detail further on in the specification, the ear plug unit comprises a pair of ear plug members mounted on the opposed ends of a generally U-shaped spring element; wherein, the ear plug members are dimensioned and designed to press the tragus of the ear inwardly to cover the auditory canal; whereby, the plug members do not penetrate the auditory canal but rather force the tragus portion of each ear to overlie the ear canal thereby blocking out sound.

BRIEF DESCRIPTION OF THE DRAWINGS

These and other attributes of the Invention will become more clear upon a thorough study of the following description of the best mode for carrying out the invention, particularly when reviewed in conjunction with the drawings, wherein:

FIG. 1 is a front perspective view of the ear plug unit being worn by a user;

FIG. 2 is a side perspective view of the ear plug unit being worn by a user;

FIG. 3 is an enlarged cross-sectional view of one end of the ear plug unit;

FIG. 4 is a top plan view of the sun shield unit fully extended; and,

FIG. 5 is a perspective view of the ear plug unit and the sun shield unit being worn by a user;

BEST MODE FOR CARRYING OUT THE INVENTION

As can be seen by reference to the drawings, and in particular to FIG. 5, the sun and sound shielding arrangement that forms the basis of the present invention is designated generally by the reference numeral (10). The arrangement (10) comprises in general an ear plug unit (11) and a sun shield unit (12). These units will now be described in seriatim fashion.

As can best be seen by reference to FIGS. 1 through 3, the ear plug unit (11) comprises a pair of ear plug members (13) disposed on opposite ends of a generally U-shaped spring element (14). The spring element (14) comprises in general a thin springy metal wire (15) having a protective coating (16) such as rubber or plastic formed on the free ends (17) of the rod (15).

In addition as is shown in FIG. 3, the ear plug members (13) comprise an inner cushion pad element (18) formed on the ends (17) of the contoured spring wire (15) and covered with a generally resilient fabric (19) such as foamed rubber, or plastic; wherein, the plug members are dimensioned to cover and overlie the tragus (101) of a users ear (100); whereby, the spring bearing effect of the wire rod (15) will fold the tragus (101) over the auditory canal (102) of the users ears (100) to block out sound in a well recognized fashion without the necessity of the plug members (13) entering the auditory canal (102).

Turning now to FIGS. 4 and 5, it can be seen that the sun shield unit (12) comprises a sun shade member (20) fabricated from a rigid yet flexible pliant sheet (21) of material having a generally German Cross configuration; and including a generally square central panel (21) having contoured arm elements (22) projecting outwardly from the sides of the panel (21) which are joined together on their outboard ends by suitable securing means (23) to form a generally open end box configuration; wherein, the sides of the box configuration are provided with arcuate air flow openings (24) which will permit air to circulate freely around the users head while they are lying down as depicted in FIG. 5.

In addition the outer surface of the sun shade member (20) is further provided with a reflective coating (25) which is employed to minimize the heat buildup within the interior of the sun shade member (20). Furthermore the sun shade member 920) is provided with an elongated strap member (26) which is adapted to cooperate with releasable fastening means (27) disposed on opposed arms (22) of the sun shade member (20); whereby the strap member (26) can provide either a capture loop for restraining movement of the sun shade member (20), or a wrapping strap for maintaining the sun shade member (20) in its collapsed disposition during storage.

Turning now to FIGS. 1,2 and 5, it can be seen that the ear plug unit (11) of the arrangement (10) is intended to engage the users ears (100) with the wire rod resting on the users throat (104). In addition when the user lies on their back one of the arm elements (22) of the sun shield member (20) will be held captive by the back of the users head; while the strap member (26) will be held captive by the users upper torso, so as to keep the sun shade member (20) from being blown away by the wind.

I claim:

1. A sun and sound shielding arrangement consisting of:

an ear plug unit comprising a pair of ear plug members disposed on opposite ends of a U-shaped spring element; wherein, the ear plug members are dimensioned to overlie and forcibly engage the tragus of each of the users ears; and each of the ear plug members comprise an inner cushion pad element formed on the ends of the spring element and covered with a resilient fabric; and, wherein the spring element exerts sufficient force on the ear plug members to flex the tragus in each ear into a position to block the auditory canal of the ear; and a sun shield unit comprising a collapsible sun shade member fabricated from a sheet of flexible, pliant material having a generally open end box configuration which is dimensioned to fit over a users head to provide shade; wherein, said sun shade member includes a generally square central panel having arm elements projecting outwardly from the sides of the said central panel; wherein, the free ends of the arm elements are provided with securing means for connecting the arm elements together to form in conjunction with the central panel said generally open end box configuration; and wherein, said sheet of material is provided with a generally German Cross configuration such that the opposed sides of the arm elements form arcuate openings on the sides of the open end box configuration when the arm elements are operatively connected to one another.

2. The combination of claim 1; wherein, said sun shade member is further provided with a reflective coating.

3. The combination of claim 1, wherein, said sun shade member is further provided with a strap member.

* * * * *